United States Patent [19]

Dereume

[11] Patent Number: 5,653,747
[45] Date of Patent: Aug. 5, 1997

[54] LUMINAL GRAFT ENDOPROSTHESES AND MANUFACTURE THEREOF

[75] Inventor: Jean-Pierre Georges Emile Dereume, Brussels, Belgium

[73] Assignee: Corvita Corporation, Miami, Fla.

[21] Appl. No.: 546,524

[22] Filed: Oct. 20, 1995

Related U.S. Application Data

[63] Continuation of Ser. No. 112,774, Aug. 26, 1993, abandoned.

[30] Foreign Application Priority Data

Dec. 21, 1992 [BE] Belgium .............................. 9201118

[51] Int. Cl.⁶ ............................................. A61F 2/06
[52] U.S. Cl. ................................... 623/1; 623/12
[58] Field of Search ........................ 623/1, 11, 12

[56] References Cited

U.S. PATENT DOCUMENTS

| | | | |
|---|---|---|---|
| 3,700,380 | 10/1972 | Kitrilakis | 623/1 |
| 4,173,689 | 11/1979 | Lyman et al. | 521/64 |
| 4,286,341 | 9/1981 | Green et al. | 623/1 |
| 4,323,525 | 4/1982 | Bornat | 264/24 |
| 4,459,252 | 7/1984 | MacGregor | 264/46.9 |
| 4,475,972 | 10/1984 | Wong | 156/167 |
| 4,512,338 | 4/1985 | Balko et al. | 128/1 R |
| 4,604,762 | 8/1986 | Robinson | 623/1 |
| 4,655,771 | 4/1987 | Wallsten | 623/1 |
| 4,712,553 | 12/1987 | MacGregor | 128/355.5 |
| 4,733,665 | 3/1988 | Palmaz | 128/343 |
| 4,738,740 | 4/1988 | Pinchuk et al. | 156/167 |
| 4,800,882 | 1/1989 | Gianturco | 128/343 |
| 4,816,028 | 3/1989 | Kapadia et al. | 623/1 |
| 4,820,298 | 4/1989 | Leveen et al. | 623/1 |
| 4,878,908 | 11/1989 | Martin et al. | 623/1 |
| 4,954,126 | 9/1990 | Wallsten | 600/36 |
| 4,994,071 | 2/1991 | MacGregor | 606/194 |
| 5,019,090 | 5/1991 | Pinchuk | 606/194 |
| 5,116,360 | 5/1992 | Pinchuk et al. | 623/1 |
| 5,156,620 | 10/1992 | Pigott | 623/1 |
| 5,171,262 | 12/1992 | MacGregor | 623/1 |
| 5,195,984 | 3/1993 | Schatz | 606/195 |
| 5,236,447 | 8/1993 | Kubo et al. | 623/1 |
| 5,360,443 | 11/1994 | Barone | 623/1 |

FOREIGN PATENT DOCUMENTS

| | | | |
|---|---|---|---|
| 793020405 | 4/1990 | European Pat. Off. | |
| 0461791A1 | 12/1991 | European Pat. Off. | |
| 3918736A1 | 12/1990 | Germany | |
| 1205743 | 9/1970 | United Kingdom | |
| 2115776 | 9/1983 | United Kingdom | |
| 9206734 | 4/1992 | WIPO | |
| 94001056 | 1/1994 | WIPO | 623/12 |
| 94013224 | 6/1994 | WIPO | 623/1 |

*Primary Examiner*—Michael J. Milano
*Attorney, Agent, or Firm*—Lockwood, Alex, Fitzgibbon & Cummings

[57] ABSTRACT

A luminal endovascular graft or endoprosthesis having a tubular support which expands between a first diameter and a second, larger diameter is provided with an expandable porous coating which is applied over either or both of the internal cylindrical surface and the external cylindrical surface of the tubular support. The first diameter allows the introduction of the luminal endoprosthesis into human or animal body passages. The expandable coating preferably is made from biocompatible fibers formed into a structure which allows normal cellular invasion upon implantation, without stenosis or restenosis, when the support element is at its second diameter.

18 Claims, 1 Drawing Sheet

LUMINAL GRAFT ENDOPROSTHESES AND MANUFACTURE THEREOF

This application is a continuation of application Ser. No. 112,774, filed Aug. 26, 1993 now abandoned.

BACKGROUND AND DESCRIPTION OF THE INVENTION

This invention generally relates to luminal graft endoprostheses or endovascular grafts which have the ability to carry out dilation and/or support functions. These devices are suitable for treating blood vessel lesions and the like. An expandable endovascular prosthesis tubular support component and elastomeric graft material are combined into a single device wherein the graft material is secured to either or both of the internal and external surfaces of the expandable endoprosthesis. The graft material preferably is produced by a spinning technique such as that described in U.S. Pat. No. 4,475,972, the subject matter thereof incorporated by reference hereinto.

In summary, the luminal graft endoprosthesis includes a tubular support with an internal surface and an external surface. It is expandable from a first diameter to a second diameter which is greater than the first. When it is in its first diameter, the tubular support is of a size and shape suitable to be inserted into human or animal body pathways. An expandable coating, made from a substantially inert biocompatible graft material is applied onto at least one of the surfaces or walls of the tubular support element.

Luminal endoprostheses with expandable coating on the surface of external walls of radially expansible tubular supports are proposed in U.S. Pat. Nos. 4,739,762 and 4,776,337. In these two patents, the manufacturing process is not described and the coating is made from thin elastic polyurethane, Teflon film or a film of an inert biocompatible material. Such film may have radially projecting ribs for fixation, and macroscopic openings, via which the blood can flow between the covering and the vessel in which the endoprosthesis is anchored. Correspondingly, a coating formed from an elastomeric polyurethane film has been applied around a metallic support with form memory properties. See A. Balko et al., "Transfemoral Placement of Intraluminal Polyurethane Prosthesis for Abdominal Aortic Aneurysm", *Journal of Surgical Research*, 40, 305–309, 1986. In U.S. Pat. Nos. 5,019,090 and 5,092,877, the possibility of covering the support of a radially expansible endoprosthesis is generally mentioned but not described.

All of the luminal endoprostheses made according to these previous approaches have the disadvantage that the material used is not sufficiently biocompatible. In fact, expansible tubular supports have existed for a long time, for example, supports used solely to keep the mouths of certain weak vessels open. It should especially be mentioned that there are supports or stents which are expanded by applying an exterior force, e.g. inflating a balloon located inside the support. See for example U.S. Pat. Nos. 4,733,665, 4,739, 762, 4,776,337, 4,800,882 and 5,019,090. As is the case with other supports, it must be noted that some of these are auto-expansible due to their elasticity (see particularly U.S. Pat. No. 4,580,568 and the supports placed onto the market by Pfizer under the WALLSTENT® name), or due to their form memory properties (supports placed onto the market under the NITINOL name).

Other prior approaches include semi-rigid prostheses introduced endoluminally. These prostheses have the form of full tubes which can be connected to vessels to be reinforced by means of end supports such as those mentioned above. See for example U.S. Pat. Nos. 4,140,126, 4,787,899 and 5,104,399 and J. C. Parodi et al., "Transfemoral Intraluminal Graft Implantation for Abdominal Aortic Aneurysms", *Annals of Vascular Surgery*, Vol. 5, No. 6, 1991.

Based on actual experience, when supports have been used alone, it has been shown that they lead to unorganized development of the cells in the mesh of the support, with rapid reforming of the cellular thickening in the vessels to be protected, i.e. fibrous hyperplasia. On the other hand, the tubes introduced as endoprostheses are used without a supporting element. Thus, a certain degree of rigidity must be offered. Their structures make them inappropriate in terms of the cellular growth on their walls. For the same reasons, expandable endoprostheses with an expandable coated support are inappropriate for normal growth of cells. They continue to represent a foreign body on the inside of the human or animal body into which they are implanted and, because of the films used, no normal cellular invasion is possible on the inside of their structure.

There are tube-formed prostheses made from fibrous material having a structure of superimposed layers of fibers, where the fibers of one layer intersect those of neighboring layers, and a manufacturing process for such prostheses has been described. See J. Leidner et al., "A Novel Process For the Manufacturing of Porous Grafts: Process Description and Product Evaluation", *Journal of Biomedical Materials Research*, Vol. 17, 229–247 (1983). These prostheses are used to replace fragments of defective vessels. Radial expansion of these prostheses is not necessary and is usually disadvantageous in view of the internal blood pressure. Generally, there are approximately 400 superimposed layers of successively interlaced fibers.

To solve these problems, in accordance with this invention, a luminal endoprosthesis is provided with an expansible coating made from fibrous material. The fibers of this fibrous material form a structure among themselves which facilitates normal cellular invasion, without stenosis or recurrent stenosis of the human or animal pathway when the supporting element is in its second or expanded diameter. Surprisingly, it has been found that fibrous material, in which the openings between the fibers are greater than 30μ, preferably at least 50μ, when the element is in its second diameter, not only facilitates cellular invasion, but also achieves particularly normal cellular growth with perfect cohabitation between cells and compatible biological fibers.

According to an implementation form of this invention, the fibers of the fibrous material are oriented at an angle less than 50°, often less than 30°, with respect to a generator of the tubular support element, when the latter is in its first diameter. Advantageously, the fibrous material is elastic. Preferably, polycarbonate fibers or polycarbonate urethane fibers are used, although other materials are possible. For example, polycarbonate polyurethane fibers placed onto the market by Corvita Corporation under the name CORETHANE® are especially suitable. When such a fibrous coating is used, the diameter of its cylinder shape can be extended by 2 to 4 times with a concommitment change in wrap angle from 30° to 50° to 50° to 90°. According to an advantageous implementation form of this invention, the fibers of the fibrous material have a diameter to 10μ to 20μ and are arranged in several superimposed layers.

According to the preferred form of this invention, the support has an expandable covering which is applied onto or adhered to the surface of the external wall of the support element and/or onto the surface of the internal wall. It is also possible to consider reinforced endoprostheses, in which the support element does not come into contact with the human or animal tissue, which embodiment is accomplished by incorporating the support structure into the wall of the graft. This results in improved biocompatibility.

The process for manufacturing an endoprosthesis according to this invention applies to an expandable, fibrous cover onto at least one of the surfaces of the wall of the support element. When the support element is at its first diameter, the device has a predetermined fibrous structure. When the support element is at its second diameter, the openings between the fibers of the fibrous material are greater than 30μ and preferably at least 50μ. This process is preferably employed when a tubular support or endoprosthesis that is expandable by an internal force is used, for example one that is deployed by inflating with a balloon.

In an alternative approach, an expandable, fibrous covering with a predetermined fibrous structure is applied to at least one of the surfaces of the wall of a support element having a third diameter, equal to or greater than its second diameter. When the support element is in its second diameter, the openings between the fibers of the fibrous material are greater than 30μ and preferably at least 50. The wrap angle in its second diameter is 40° to 70°. The thus covered support element is longitudinally stretched to its first diameter where the wrap angle is reduced to 20° to 30° and introduced to the body in this first diameter configuration. Introduction is performed by pushing the longitudinally stretched structure out of the lumen of a catheter, at which point the structure self expands to its second diameter. This approach is especially suitable when a self-expanding or auto-expandable, such as a spring-loaded type, of tubular support is used.

BRIEF DESCRIPTION OF THE DRAWINGS

Other details and particularities of the invention emphasizing the claims and a description are given in a non-limiting matter with reference to the accompanying drawings wherein the identical or analogous elements on these figures are designated by the same references:

DETAILED DESCRIPTION OF THE INVENTION

Figure 1:
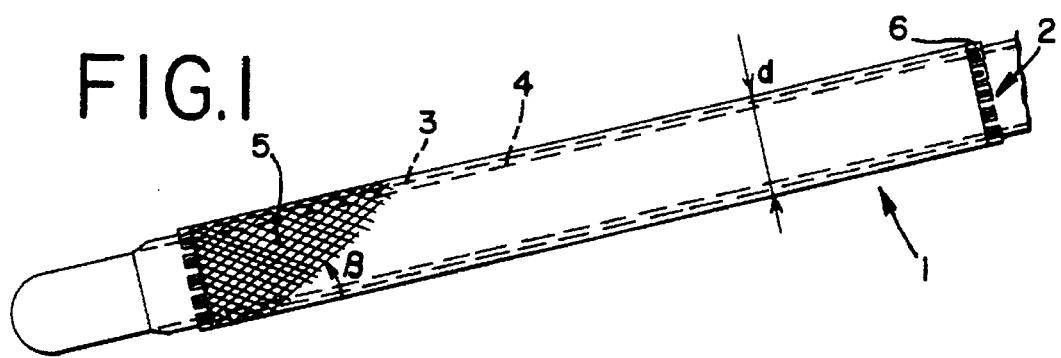
FIG. 1 shows a form of the luminal endoprosthesis in accordance with the invention, in which form the luminal endoprosthesis can be introduced into human or animal body pathways.
Figure 2:
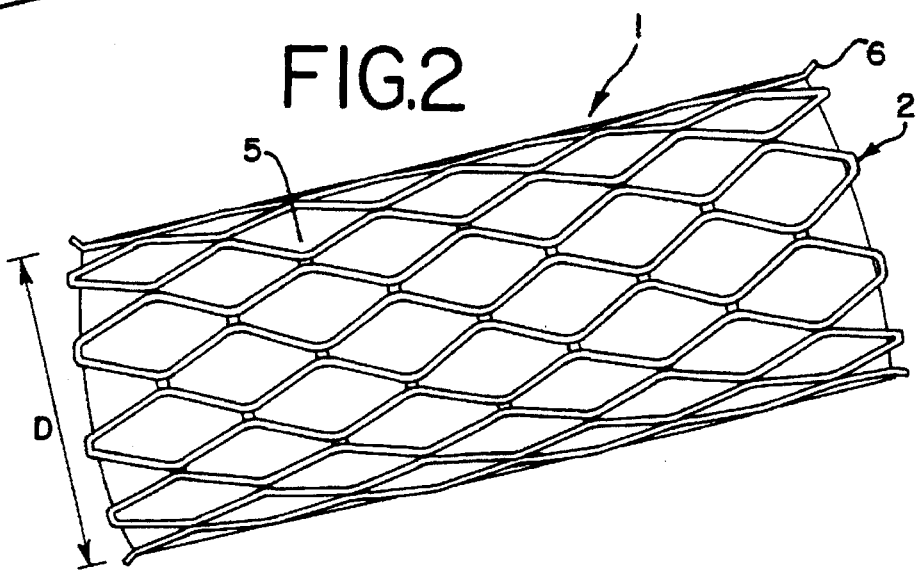
FIG. 2 shows the luminal endoprosthesis illustrated in FIG. 1 after radial expansion.

FIGS. 1 and 2 illustrate a luminal endoprosthesis according to this invention. This endoprosthesis has a tubular support 2 expansible from a first diameter d as shown in FIG. 1 to a second diameter D as shown in FIG. 2. When the support is in its first diameter, it can be introduced into human or animal body pathways, for example, into peripheral blood vessels and then lead to the desired site. There, the support is expanded to its second diameter D. It is to be noted that the second diameter D is not necessarily the maximum expansion diameter of the support, but that corresponding to its application against the walls of the human or animal body pathway to be supported at the desired site. Thus, the support may also have a third diameter, greater than the second.

The tubular support used in the illustrated example is a support that is inflated by an internal balloon 3, and represented in broken line in FIG. 1. The balloon 3 is mounted onto a catheter 4. With this structure, the luminal endoprosthesis can be expanded from an insertion configuration to an implanted configuration by radially outwardly directed forces imparted by the balloon 3. An autoexpandable tubular support is also possible, in which case, the support is surrounded by a sleeve which keeps it in the first diameter d until the device is positioned for deployment such as from the end of a catheter to its expanded state.

The luminal endoprosthesis in accordance with the invention also has an expandable coating 5, made from inert biocompatible material, applied onto the surface of the external wall and/or the internal wall of the support. This cover is porous and preferably made from fibrous material. The openings between the fibers are greater than 10μ, preferably between about 30μ and 100μ, when the support is in the state as shown in FIG. 2.

As shown in FIG. 1 with a balloon-expandable support, when the diameter of support 2 is equal to d, the fibers of the expandable coating are oriented at an angle β of approximately 30° with respect to the longitudinal axis of the tubular support. Depending on the desirable expansion between the first diameter d and the second diameter D, i.e. depending on the radial expansion on the endoprosthesis, angle β will be variable. After radial expansion, diameter D will preferably be between 2 and 4 times the initial diameter d. When the support reaches diameter D, the fibers are reoriented with respect to one another, and the angle between them and the longitudinal axis increases. In this position, this angle, for example, may have reached 45° or greater, for example 90°.

The porous material need not be elastomeric, although this is advantageous and highly preferred. Preferred fibers are polyurethane fibers. A particularly suitable polyurethane is a polycarbonate urethane available from Corvita Corporation under the CORETHANE® trademark and described in U.S. Pat. Nos. 5,133,742 and 5,229,431, incorporated by reference hereinto. Fibers of these polycarbonate urethanes are especially crack-resistant yet elastomeric and pliable. It will be appreciated that the elasticity of fibers facilitates the expanding property of the cover or expandable coating.

In the manufacturing example, the expandable coating is made from polycarbonate urethane fibers having a diameter of 10μ to 20μ and arranged in several layers, e.g. 100 or more superimposed layers. The fibers of one layer are parallel to one another. The fibers of the respective upper neighboring layer and the lower neighboring layer are parallel to one another but they intersect the fibers of the respective neighboring layer. The fibers are bonded among themselves at the sites of crossing. Due to this arrangement, radial expansion is possible as long as the number of superimposed layers is not excessive, i.e. there are not more than about 500 layers. Moreover, owing to this, the desired opening between the fibers develops when the covering is expanded.

The expandable porous coating or elastomeric graft component preferably is produced by a spinning technique such as that described in U.S. Pat. No. 4,475,972, incorporated by reference hereinto. Polymer in solution is extruded into fibers from a spinnerette onto a rotating mandrel. The spinnerette system is reciprocated along the longitudinal axis of the mandrel at a controlled pitch angle, resulting in a non-woven structure where each fiber layer is bound to the underlying layer. Control of the pitch angle allows for control of compliance and kink resistance of the graft component. A layer of polymer fibers can be spun onto the mandrel and the tubular support 2 slid over this layer. Alternatively, the tubular support 2 may be applied directly onto the mandrel with a layer of polymer fibers spun thereover. It is also possible to spin a layer of fibers onto the mandrel, apply the tubular support 2 over this layer, and then spin an additional layer of fibers over the tubular support such that it is coated with fibers on both its inner and outer surfaces. Bonding the inner and/or the outer layers of fibers to the tubular support 2 and/or to each other may be achieved by thermal bonding and/or by the use of adhesive agents such as an adhesive, a hot melt adhesive, a silicone adhesive, a primer, a coupling agent, combinations thereof, and the like.

As can be seen in FIG. 1, the two end zones 6 of the support 2 are not covered. When the support reaches its second diameter D, its expansion is limited in its central part by the cover 5, but the expansion of the end zones 6 is not limited. Thus, under these conditions, the end zone portions 6 of the support radially project toward the outside and, therefore, can serve as anchoring fixation members onto the wall of the body pathway to be supported.

While not preferred, in certain instances, the porous coating not only can be made from spun or non-woven material as described but also from woven or knitted material. Moreover, one surface of the internal wall of the support may be covered or the covering can be applied to both surfaces of the wall of the support. In the latter case, the support no longer comes into immediate contact with the tissue of the human or animal body.

Preferably, the fibers in each of the above-mentioned superimposed layers are oriented in such a manner that they intersect the fibers of a neighboring upper layer and those of the lower neighboring layer. By adapting the manufacturing process of Leidner and of U.S. Pat. No. 4,475,972, it has been found to be possible to directly apply a highly expandable cover, also formed from crossed superimposed layers of fibers, onto an expandable tubular support.

As mentioned above, endoprostheses made according to this invention can be introduced into peripheral blood vessels and advanced to the artery or vein, where the opening has been obstructed, for example, by exaggerated cicatrization (healing), abnormal cellular growth (fibrous hyperplasia) or arterial or venous stenosis. Moreover, these endoprostheses can be used to reinforce vascular walls, weakened by pathological processes, for example, by parietal or dilated dissection, as in the case of aneurysms. In addition, they can also obliterate congenital or acquired arteriovenous communications. They can be applied in intrahepatic portal-caval shunts. These endoprostheses can also be used to keep other biological pathways open, for example digestive, biliary, pancreatic, urinary tracts. They help to limit the intraluminal growth of pathological processes, such as fibrosis or cancer.

One primary and unexpected advantage of these endoprostheses in accordance with this invention is the fact that transparietal invasion of the covering by living tissue is possible without unorganized cellular development and tendency towards stenosis or recurrent stenosis.

A mode of application of an endoprosthesis in accordance with the invention will be described below by means of non-limiting examples.

EXAMPLE 1

A communication is surgically created between the aorta and the inferior vena cava of dogs. This communication is closed by opening the femoral artery of the dog and inserting a catheter with a dilatable balloon into it. An endoprosthesis according to this invention is mounted onto the catheter, as described in FIG. 1. This unit, having a diameter of 3 or 4 mm is subjected to angioscopic control where the aortal-caval fistula has been created. By inflating the balloon, the diameter of the endoprosthesis can be expanded to 12 mm with the open ends of the support being pressed into the aortic wall, thus suppressing the aortal-caval fistula. Then, the balloon is deflated and removed from the body with the catheter.

After one month, the endoprostheses were explanted at the implantation site. Via direct examination and a study of histological sections, it can be determined whether the endoprosthesis has been completely invaded by living tissue, in particular its coating and whether endothelial cells have re-established on the luminal face. In fact, a collagenous luminal deposit covered by a layer of neoendothelial cells has been observed at the surface in contact with blood.

The stripes of the support provided with coating are surrounded by collagen and covered by neointima. The histological signs of rejection or fibrous hyperphasia responsible for the clinical setbacks observed with endoprostheses made by previous methods were not seen here. No huge foreign body cells and no macrophages were observed.

EXAMPLE 2

Figure 3:
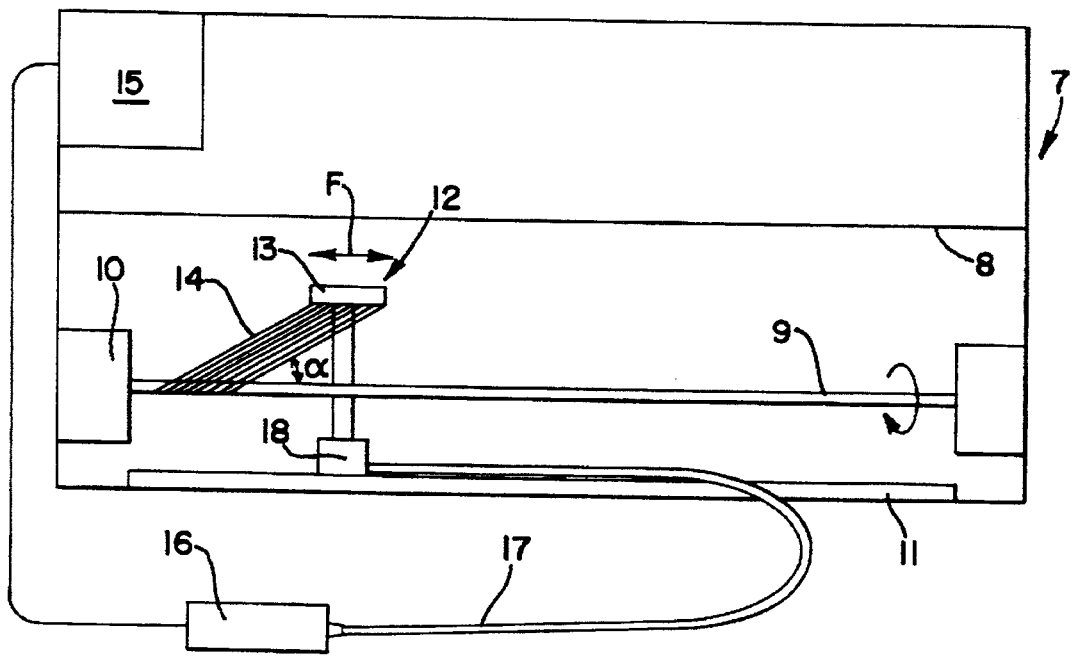
FIG. 3 shows a device used to manufacture preferred luminal endoprostheses according to this invention.

FIG. 3 illustrates a device for use in the manufacture of endoprostheses according to this invention. This device roughly corresponds to the one described by J. Leidner et al., op. cit. It consists of a frame supporting a closed chamber. An elevated temperature is maintained inside the chamber. Owing to this, the fibers can be bonded when they are applied. A mandrel 9 rests inside the chamber. The diameter of this mandrel is just smaller than the diameter d of the expandable support. A rotative motor causes this mandrel 9 to rotate around its longitudinal axis. Moreover, the chamber 9 contains a rail 11, arranged parallel to the mandrel 9. A die, generally designated by reference numeral 12, can slide back and forth in direction F. This die 12 is led onto the rail 11 by a motor 18. The extruder head 13 is arranged just above the mandrel 9 and has several openings via which the filaments of the extruded material can leave. This material comes from a container 15, from which it is pumped by a pump 16 under pressure into a flexible conduit 17 which opens onto the base of the die 12. A cooling jacket, not shown in detail, keeps the temperature of the extrusion material, here polycarbonate urethane in a solvent, at the discharge of the die, at 35° C.

A support 2 in its first diameter is led onto the mandrel 9 and is brought into rotation by the latter. When desired, the support can be directly placed at the site of the mandrel. The die 12 is reciprocated (back and forth), and the filaments extruded by the die leave it at a certain angle α of inclination with respect to the mandrel axis. This angle can be adjusted as a function of the speed of the die and the rotational speed of the motor 10.

When the die 12 reaches the end of the mandrel 9, at the right on FIG. 3, its displacement direction has been reversed, in a known manner, by motor 18, and the extruded filaments are inclined by angle α with respect to the mandrel, but opposite to that of the first layer. Thus, the fibers of the second layer are parallel to one another but cross those of the first layer. The following manufacturing parameters were used in this non-limiting example:

| | |
|---|---|
| Temperature of the material extruded at the outlet of the extruder head | 35° C. |
| Temperature of the material inside of the chamber 8 | 40–70° C. |
| Relative air humidity in the enclosed space | <40% |
| Diameter of the mandrel | 3 mm |
| Angle of inclination of the fibers with respect to the mandrel axis | 30° |
| Speed of the linear motor 18 | 19.8 cm/s |
| Flow of the fibers | 0.061 ml/min. |
| Speed of the fibers | 30.8 cm/s |
| Rotational speed of the mandrel | 1500 rpm |
| Number of layers | 200 layers |

Alternatively, the fibrous layer can be spun at a high pitch angle of 80° representing expanded diameter D. The fibrous tube can then be pulled longitudinally such that the diameter is that of d. The tube can be heat set in this configuration, then placed over the support.

As another alternative, before placing the support onto the mandrel 9, several layers of fiber can be applied directly onto the mandrel as described, and then the support is placed onto the mandrel in accordance with the manufacturing process previously described. In this case, the surface of the external wall and the surface of the internal wall of the support are covered.

After discharge from the enclosed space of the closed chamber, the coated supports made in accordance with the selected procedure are cut into desired lengths.

EXAMPLE 3

A procedure along the lines of Example 2 was carried out to use an auto-expansible support. The mandrel 9 has a diameter just below the maximum diameter of the support, and this is placed onto the latter. The parameters of the Example 2 process were modified to take into consideration the fact that, in this form, the support will be stretched until it reaches its diameter d. Therefore, the angle α must be much larger, for example, 50° or greater, perhaps almost 90°, so that after expansion, an angle of 30° can be obtained between the fibers and the generator of the support. When the support is stretched, the fibers are rearranged among themselves by reducing the above-mentioned angle and thanks to their visco-elasticity, if they are elastic. As a result, there is no crumpling or crinkling of the covering around the support during stretching.

More specifically, 16 mm internal diameter self-expanding Wallstent®, 15 cm long, formed of 24 helically wound wires at 50° wrap angle in respect to the longitudinal axis of the stent, was incorporated into the wall of an endoprosthesis in the following manner: First, the Wallstent® was prepared by dipping it into a dilute solution of a low melting point adhesive (100° C.) and then the adhesive was dried where it forms a thin layer or coating of adhesive on the wire stent.

The mesh was prepared by spinning 400 layers of polycarbonate urethane fibers from dimethylacetamide solution (45% solids content) onto a 16 mm diameter mandril, at a 50° wrap angle, at a flow rate of 0.085 ml/min at 500 rpm. The fibers were then dried at room temperature on the mandril. When dry, the fibrous mesh, still on the mandril is rotated, and 3 cm long sections of fibrous mesh were cut with a razor blade and removed every 13 cm along the length of the graft. A multiplicity of Wallstents® equal to the number of 13 cm lengths of mesh were slightly compressed longitudinally and slid over and placed on the 13 cm lengths of meshed mandril such that 1 cm on each end of the stent was exposed to bare mandril. An additional 100 layers of fiber were spun on the external wall of the endoprosthesis. The endoprosthesis on the mandril was then dried, annealed and heat bonded to the metal and between mesh layers, followed by cooling and removal from the mandril.

While the present invention has been described with particularity, it is the intent that the invention include all modifications and alternations from the disclosed embodiments that fall within the spirit and scope of the appended claims.

I claim:

1. A luminal endoprosthesis for deployment within a living body pathway, comprising:

a tubular expandable support element with a longitudinal axis, an external generally cylindrical surface and an internal generally cylindrical surface, said support element being expandable from a first diameter at which it is adapted to be inserted into a living human or animal body pathway a second diameter, the second diameter being greater than the first diameter, said expandable support element being capable of supporting walls of the living body pathway when at the second diameter, said second diameter being 1.5 to 12 times greater than said first diameter of the expandable support element;

an expandable porous coating made from an essentially inert biocompatible material, said expandable coating being applied over at least one of said external and internal generally cylindrical surfaces of the expandable support element;

said tubular expandable support element extending substantially the full length of the expandable porous coating;

the expandable coating is made from porous material having pores that open when the tubular support element expands from said first diameter to said second diameter to provide open pores which allow normal cellular invasion thereinto from the body pathway when implanted therewithin;

said expandable porous coating is an elastomeric fibrous material of elastomeric fibers, said fibers being essentially inert and each is linear and oriented at an angle $\beta$ with respect to the longitudinal axis of the tubular support element when at its first diameter, said angle $\beta$ being less than about 80°;

said elastomeric fibers being arranged in a plurality of at least 10 layers of superimposed fibers, each fiber of which extends substantially the length of said tubular support element, with the fibers in each of the superimposed layers being oriented in such a manner that they cross the fibers of at least an upper neighboring layer or at least a lower neighboring layer in order to provide crossed fibers; and said crossed fibers reorient with respect to one another when the tubular support element expands such that said angle $\beta$ of each fiber increases and thereby defines said pores that open when the tubular support element expands from said first diameter to said second diameter and that are thus oriented to allow said normal cellular invasion.

2. The luminal endoprosthesis in accordance with claim 1, further including openings between the fibers of fibrous material when the support is at its second diameter, said openings being greater than about 1μ.

3. The luminal endoprosthesis in accordance with claim 2, wherein said openings are at least about 10μ.

4. The luminal endoprosthesis in accordance with claim 2, wherein said openings are between about 30μ and about 100μ.

5. The luminal endoprosthesis in accordance with claim 1, wherein said angle β is less than about 30°.

6. The luminal endoprosthesis in accordance with claim 1, wherein said fibers of the fibrous material are polycarbonate urethane.

7. The luminal endoprosthesis in accordance with claim 1, wherein the fibers of the fibrous material have a diameter of about 1μ to about 30μ.

8. The luminal endoprosthesis in accordance with claim 1, wherein the expandable coating has between about 50 and about 300 layers of superimposed fibrous material.

9. The luminal endoprosthesis in accordance with claim 1, wherein the expandable coating is applied onto the external generally cylindrical surface of the support element.

10. The luminal endoprosthesis in accordance with claim 1, wherein the expandable coating is applied onto the internal generally cylindrical surface of the support element.

11. The luminal endoprosthesis in accordance with claim 1, wherein the expandable coating is applied onto both the external generally cylindrical surface and the internal generally cylindrical surface of the support element.

12. The luminal endoprosthesis in accordance with claim 1, wherein the support element has two axially extending ends, at least one of which is without said expandable coating and extends axially beyond the expandable coating.

13. The luminal endoprosthesis in accordance with claim 12, wherein said at least one axially extending end of the support element projects radially outward when the support element is in its second diameter, whereby said axially extending end serves as a member for the fixation of the endoprosthesis into the body pathway.

14. The luminal endoprosthesis in accordance with claim 1, wherein the support element is expanded by applying an outwardly directed radial force thereto.

15. The luminal endoprosthesis in accordance with claim 1, wherein the support element is auto-expandable.

16. The luminal endoprosthesis in accordance with claim 1, wherein the expandable coating is adhered to the support element.

17. The luminal endoprosthesis in accordance with claim 1, wherein the expandable coating is adhered to the support element by an adhering agent selected from the group consisting of an adhesive, a hot melt adhesive, a silicone adhesive, a primer, a coupling agent, and combinations thereof.

18. The luminal endoprosthesis in accordance with claim 1, wherein the support element is encapsulated between one said expandable coating over the external generally cylindrical surface of the support element and another said expandable coating over the internal generally cylindrical surface of the support element.

* * * * *

UNITED STATES PATENT AND TRADEMARK OFFICE
CERTIFICATE OF CORRECTION

PATENT NO. : 5,653,747
DATED : Aug. 5, 1997
INVENTOR(S) : Dereume

It is certified that error appears in the above-identified patent and that said Letters Patent is hereby corrected as shown below:

Col. 3, line 24, "50" should read --50µ--.
Col. 8, line 22, insert --and-- after "pathway".

Signed and Sealed this

Twenty-ninth Day of June, 1999

Attest:

Q. TODD DICKINSON

*Attesting Officer*   Acting Commissioner of Patents and Trademarks